US006303369B1

(12) United States Patent
Spana et al.

(10) Patent No.: US 6,303,369 B1
(45) Date of Patent: Oct. 16, 2001

(54) PROTEIN EXPRESSION SYSTEM

(76) Inventors: Carl Spana, 912B Village Dr. East, North Brunswick, NJ (US) 08902; Joseph Fargnoli, 367 Cafferty Rd., Tinicum, PA (US) 18947; Joseph B. Bolen, 4 Hamilton Ct., Lawrenceville, NJ (US) 08648

( * ) Notice: Subject to any disclaimer, the term of this patent is extended or adjusted under 35 U.S.C. 154(b) by 0 days.

(21) Appl. No.: 08/129,722

(22) Filed: Sep. 30, 1993

(51) Int. Cl.[7] .......................... C12N 15/63; C07H 21/04
(52) U.S. Cl. ...................... 435/320.1; 536/23.1; 536/24.2
(58) Field of Search ................. 435/69.1, 240.2, 435/320.1; 536/23.1, 24.2

(56) References Cited

FOREIGN PATENT DOCUMENTS

A-O 293-249    11/1988   (EP) .
9116353    *    10/1991   (WO) .

OTHER PUBLICATIONS

Peng et al. (1993), Protein Expression and Purification 4(2): 95–100 (Abstract only).*
Ausubel et al. (1992), Short Protocols in Molecular Biology, 2nd Ed. (John WIley + Sons), pp. 16–28 to 16–48.*
A. Davies et al., Biotechnology, vol. 11, Aug. 1993, pp. 933–936.
C. Spana, Protein Expression and Purification, vol. 4, No. 5, Oct., 1993, pp. 390–397.
J. A. Cooper, Peptides and Protein Phosphorylation (Kemps. B.E., ed), CRC Press, pp. 85–113, 1990.
J. A. Bolen et al., TIBS, vol. 14, pp. 404–407, 1989.
C. E. Rudd, Immunology Today, vol. 11, No. 11, pp. 400–406, 1990.
A. S. Shaw et al., Molecular and Cellular Biology, vol. 10, No. 5, pages 1853–1862, 1990.
C. Doyle et al., Nature, vol. 330, pp. 256–259, 1987.
A. M. Norment et al., Nature, vol. 336, pp. 79–81, 1988.
M. Hatakeyama et al., Science, vol. 252, pp. 1523–1528, 1991.
M. D. Summers et al., A Manual for Baculovirus Vectors and Insect Cell Culture Procedures, Texas A&M Bulletin No. 1555, pp. 10–39, 1987.
S. E. Ramer et al., Proc. Natl. Acad. Sci. USA, vol. 88, pp. 6254–6258, 1991.
J. D. Watts et al., Journal of Biological Chemistry, vol. 267, No. 2, pp. 901–907, 1991.
D. B. Smith et al., Gene, vol. 67, pp. 31–40, 1988.
J.D. Marth et al., Cell, vol. 43, pp. 393–404, 1985.
V. A. Lukow etr al., Virology, vol. 167, pp. 56–71, 1988.

* cited by examiner

Primary Examiner—Robert A. Schwartzman
(74) Attorney, Agent, or Firm—Joan E. Switzer; Thomas R. Savitsky (57) ABSTRACT

An expression system for producing and isolating large quantities of protein. The system comprises an expression vector containing a first coding region which codes for glutathione-S-transferase operatively connected to a baculovirus promoter, a second coding region in-frame with the first coding region, and a restriction region downstream of the first coding region, into which the second coding region is inserted. A fusion protein encoded by the first and second coding region is produced by expression of the vector. Examples of this second coding region include Lck, LynB, Syk, Blk, Fyn, and Yes. A process for expression of the vector in a host cell such as *Spodoptera frugiperda* is also included.

4 Claims, 6 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
    (A) LENGTH: 693 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..693

(xi) SEQUENCE DESCRIPTION: SEQ ID NO:1:

```
ATG TCC CCT ATA CTA GGT TAT TGG AAA ATT AAG GGC CTT GTG CAA CCC       48
Met Ser Pro Ile Leu Gly Tyr Trp Lys Ile Lys Gly Leu Val Gln Pro
  1               5                  10                  15

ACT CGA CTT CTT TTG GAA TAT CTT GAA GAA AAA TAT GAA GAG CAT TTG       96
Thr Arg Leu Leu Leu Glu Tyr Leu Glu Glu Lys Tyr Glu Glu His Leu
                 20                  25                  30

TAT GAG CGC GAT GAA GGT GAT AAA TGG CGA AAC AAA AAG TTT GAA TTG      144
Tyr Glu Arg Asp Glu Gly Asp Lys Trp Arg Asn Lys Lys Phe Glu Leu
             35                  40                  45

GGT TTG GAG TTT CCC AAT CTT CCT TAT TAT ATT GAT GGT GAT GTT AAA      192
Gly Leu Glu Phe Pro Asn Leu Pro Tyr Tyr Ile Asp Gly Asp Val Lys
 50                  55                  60

TTA ACA CAG TCT ATG GCC ATC ATA CGT TAT ATA GCT GAC AAG CAC AAC      240
Leu Thr Gln Ser Met Ala Ile Ile Arg Tyr Ile Ala Asp Lys His Asn
 65                  70                  75                  80

ATG TTG GGT GGT TGT CCA AAA GAG CGT GCA GAG ATT TCA ATG CTT GAA      288
Met Leu Gly Gly Cys Pro Lys Glu Arg Ala Glu Ile Ser Met Leu Glu
                 85                  90                  95

GGA GCG GTT TTG GAT ATT AGA TAC GGT GTT TCG AGA ATT GCA TAT AGT      336
Gly Ala Val Leu Asp Ile Arg Tyr Gly Val Ser Arg Ile Ala Tyr Ser
            100                 105                 110

AAA GAC TTT GAA ACT CTC AAA GTT GAT TTT CTT AGC AAG CTA CCT GAA      384
Lys Asp Phe Glu Thr Leu Lys Val Asp Phe Leu Ser Lys Leu Pro Glu
            115                 120                 125

ATG CTG AAA ATG TTC GAA GAT CGT TTA TGT CAT AAA ACA TAT TTA AAT      432
Met Leu Lys Met Phe Glu Asp Arg Leu Cys His Lys Thr Tyr Leu Asn
130                 135                 140

GGT GAT CAT GTA ACC CAT CCT GAC TTC ATG TTG TAT GAC GCT CTT GAT      480
Gly Asp His Val Thr His Pro Asp Phe Met Leu Tyr Asp Ala Leu Asp
145                 150                 155                 160

GTT GTT TTA TAC ATG GAC CCA ATG TGC CTG GAT GCG TTC CCA AAA TTA      528
Val Val Leu Tyr Met Asp Pro Met Cys Leu Asp Ala Phe Pro Lys Leu
                165                 170                 175

GTT TGT TTT AAA AAA CGT ATT GAA GCT ATC CCA CAA ATT GAT AAG TAC      576
Val Cys Phe Lys Lys Arg Ile Glu Ala Ile Pro Gln Ile Asp Lys Tyr
            180                 185                 190

TTG AAA TCC AGC AAG TAT ATA GCA TGG CCT TTG CAG GGC TGG CAA GCC      624
Leu Lys Ser Ser Lys Tyr Ile Ala Trp Pro Leu Gln Gly Trp Gln Ala
            195                 200                 205

ACG TTT GGT GGT GGC GAC CAT CCT CCA AAA TCG GAT CTG GTT CCG CGT      672
Thr Phe Gly Gly Gly Asp His Pro Pro Lys Ser Asp Leu Val Pro Arg
            210                 215                 220

GGA TCC CCG GGA ATT CAT CGT                                          693
Gly Ser Pro Gly Ile His Arg
225                 230
```

(2) INFORMATION FOR SEQ ID NO:2:

(i) SEQUENCE CHARACTERISTICS:
        (A) LENGTH: 231 amino acids (B) TYPE: amino acid
        (D) TOPOLOGY: linear (ii) MOLECULE TYPE: protein (xi) SEQUENCE DESCRIPTION: SEQ ID NO:2:

Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
             35                  40                  45

Gly Leu Glu Phe Pro Asn Leu Pro Tyr Tyr Ile Asp Gly Asp Val Lys
         50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
        210                 215                 220

Gly Ser Pro Gly Ile His Arg
225                 230

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TATAAATATG TCCCCTATAC TA                                                    22

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CGTCAGTCAG TCACGAT                                                    17

(2) INFORMATION FOR SEQ ID NO:5:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO:5:

CTG GTT CCG CGT GGA TCC CGG GTA CCT TCT AGA ATT CCG GAG CGG CCG      48
Leu Val Pro Arg Gly Ser Arg Val Pro Ser Arg Ile Pro Glu Arg Pro
 1               5                  10                  15

CTG CAG ATC T                                                         58
Leu Gln Ile (2) INFORMATION FOR SEQ ID NO:6:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:6:

Leu Val Pro Arg Gly Ser Arg Val Pro Ser Arg Ile Pro Glu Arg Pro
 1               5                  10                  15

Leu Gln Ile (2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO:7:

CTG GTT CCG CGT GGA TCC CCG GGA ATT CCT CTC TAC ATT CCT TCA GGG      48
Leu Val Pro Arg Gly Ser Pro Gly Ile Pro Leu Tyr Ile Pro Ser Gly
 1               5                  10                  15

ATC ATG GGC                                                           57
Ile Met Gly (2) INFORMATION FOR SEQ ID NO:8:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:8:

```
Leu Val Pro Arg Gly Ser Pro Gly Ile Pro Leu Tyr Ile Pro Ser Gly
 1               5                   10                  15
Ile Met Gly
```

PROTEIN EXPRESSION SYSTEM

FIELD OF THE INVENTION

The present invention relates to processes for expression of proteins and to expression vectors and host cells used therefor.

BACKGROUND OF THE INVENTION

The lck gene product, p56$^{lck}$, is a member of the src family of protein tyrosine kinases. Cooper, J. A. (1990) in *Peptides and Protein Phosphorylation* (Kemps, B. E., ed) pp. 85–113, CRC Press, Boca Raton, Fla. The lck protein is normally expressed in T lymphocytes and natural killer cells, where it likely performs a variety of functions relating to signal transduction through ligand binding to selected surface proteins. Bolen, J. A., and Veillette, A. (1989) *Trends Biochem. Sci.* 14, 404–407; Rudd, C. E. (1990) *Immunol. Today* 11, 400–406. In T-cells, p56$^{lck}$ forms a non-covalent complex with the CD4 and CD8a. Veillette, A., Bookman, M. A., Horak, E. M., and Bolen, J. A. (1988). For this reason, p56$^{lck}$ is believed to aid in mediation of signals emanating from the T-cell antigen receptor through ligation of CD4 or CD8 to non-polymorphic determinants on antigen-bearing major histocompatibility molecules. Shaw, A. S., Chalupny, J., Whitney, J. A., Hammond, C., Amrein, K. E., Kavathas, P., Sefton, B. M., and Rose, J. K., (1990) *Mol. Cell. Biol.* 10, 1853–1862; Doyle, C., and Strominger, J. L. (1987) *Nature* 330, 256–259; Norment, A. M., Salter, R. D., Parham, P., Engelhard, V. H., and Littman, D. R. (1988) *Nature* 336, 79–81. More recently, p56$^{lck}$ has been implicated as a signaling component of the high affinity interleukin-2 receptor. Hatakeyama, M., Kono, T., Kobayashi, N., Kawahara, A., Levin, S. D., Perlmutter, R. M., and Tanaguchi, T. (1991) *Science* 252, 1523–1528.

A better understanding of the structure and regulation of p56$^{lck}$ and similar proteins would clearly contribute to our knowledge of early signal transduction events and a source of large quantities of purified p56$^{lck}$ would be useful. While early analysis of p56$^{lck}$ functions have been greatly facilitated by antibodies directed against this protein, immunoaffinity purification has been hampered by lack of an abundant source of enzyme. This difficulty has been addressed in part by baculovirus expression systems. Summers, M. D., and Smith, G. E. (1987). *A Manual for baculovirus vectors and insect cell culture procedures*, Texas A&M bulletin No. 1555, (College Station, Texas Agricultural Experimental Station and Texas A&M University), 10–39. Recent studies using a baculovirus expression system have reported significant purification of p56$^{lck}$ using conventional chromatography methodologies. Ramer S. E., Winkler, D. G., Carrera, A., Roberts, T. M., and Walsh, C. T. (1991) *Proc. Natl. Acad. Sci. USA* 88, 6254–6258; Watts, J. D., Wilson, G. M., Ettehadieh, E., Clark-Lewis, I., Kubanek, C., Astell, C. R., Marth, J. D., and Aebersold, R, (1991) *J. Biol, Chem.* 267, 901–907. While this approach results in purified enzyme, multiple column enzyme purification is costly, time-consuming, and requires large amounts of starting material.

Glutathione-s-transferase (Gst) is a protein well known to bind to glutathione (Smith, D. B., and Johnson, K. S. (1988) *Gene* 67, 31–40). Glutathione resin may be used in column chromatography. The above baculovirus expression systems, however, do not employ Gst.

BRIEF DESCRIPTION OF THE INVENTION

The present invention relates to processes for expressing isolated forms of proteins and to expression vectors and host cells useful for such processes. In particular, this invention relates to an expression vector, comprising:

(a) a first coding region, which codes for a polypeptide capable of binding to gluthathione, operatively connected to a promoter, (b) a second coding region in-frame with the first coding region, and (c) at least one restriction site between the first and second coding regions;

wherein a fusion protein of the first and second coding regions would result from expression of the vector. Vectors derived from baculovirus are preferred.

Further in accordance with this invention is a host cell comprising such a vector. The preferred host cell is a *Spodoptera frugiperda* cell, particularly an Sf9 cell, although other host cells are suitable (see below).

Such vectors and host cells are useful in a process for expressing a protein in isolated form, which comprises:

(a) treating such a host cell under conditions allowing expression of the vector, whereby a fusion protein of the first and second coding regions will be expressed;

(b) exposing proteins from the host cell to glutathione resin, whereby the fusion protein will adhere to the resin; and (c) cleaving the expression product of the second coding region from the resin-bound fusion protein.

Further in accordance with the present invention is a process for expressing a nucleic acid sequence, which comprises:

(a) inserting the nucleic acid sequence into a baculovirus expression vector in-frame with a first coding region for a polypeptide capable of binding to glutathione, wherein the coding region is operatively linked to a promoter;

(b) placing the vector into a host cell;

(c) treating the host cell under conditions allowing expression of the vector, resulting in expression of a fusion protein of the first coding region and the sequence inserted in step (a);

(d) exposing proteins from the host cell to glutathione resin, whereby the fusion protein adheres to the resin; and (e) treating the adhered fusion protein with a protease to release the expression product of the nucleic acid sequence from the resin.

For the first coding region, the inventors prefer a sequence encoding glutathione-s-transferase (nucleotide SEQ. ID. NO.: 1; amino acid SEQ. ID. NO.: 2) or a fragment thereof capable of binding to glutathione. This system combines the high level expression of foreign proteins with baculovirus vectors (e.g., in Sf9 cells) and the ability of Gst fusion proteins to bind to glutathione resin. Treatment of the glutathione-binding fusion protein with a proteolytic substance such as thrombin can thus liberate the desired protein from the glutathione-binding portion of the fusion protein. The glutathione-binding portion remains bound to the resin, thus purifying the desired protein.

This expression system presents advantages over other systems, because it allows the practitioner (1) to produce large quantities of protein, (2) to purify significant amounts of active protein by a single chromatography step, (3) to use a wide range of extraction conditions, including non-denaturing detergents to maintain protein function, (4) to use anti-Gst antibodies, allowing for screening of recombinant baculoviruses that express cloned sequences to which antibodies have not been generated or proteins whose function can not be measured, (5) to use a multiple cloning site with many restriction sites for convenient ligation, and (6) to use and/or study thrombin because it includes a thrombin cleavage site.

DETAILED DESCRIPTION OF THE INVENTION

The following definitions apply to the terms as used throughout this specification, unless otherwise limited in specific instances.

The term "fusion protein" refers to a protein or polypeptide that has an amino acid sequence having portions corresponding to amino acid sequences from two or more proteins. The sequences from two or more proteins may be full or partial (i.e., fragments) of the proteins. Such fusion proteins may also have linking regions of amino acids between the portions corresponding to those of the proteins. Such fusion proteins may be prepared by recombinant methods, wherein the corresponding nucleic acids are joined through treatment with nucleases and ligases and incorporated into an expression vector. Preparation of fusion proteins is generally understood by those having ordinary skill in the art.

The phrase "polypeptide capable of binding to glutathione" refers to proteins, protein fragments, and synthetic polypeptides capable of binding to glutathione. Examples include glutathione-s-transferase and fragments thereof. Suitable fragments may be generated by gene amplification using 5' and 3' primers before translation or by proteolytic cleavage (see Table 2) after translation.

The term "coding region" refers to an open reading frame; i.e., a portion of a nucleic acid that has a sequence that would be translated to form a sequence of amino acids. The term "coding region" includes sequences of naturally occurring proteins as well as sequences resulting from modifications (insertions, deletions, mutations, disruptions) obtained through recombinant methods.

The term "linking region" refers to a sequence of amino acids between coding regions from different sources in a fusion protein. Typically, linking regions encode sites recognized by proteases and thus allow the expression products of the coding regions to be separated from each other.

The phrase "operatively linked to a promoter" means that the promoter is capable of directing the expression of the associated coding region. Coding regions for the fusion protein may also be operatively linked to other regulatory elements, such as enhancers.

The preferred embodiment employs a Gst sequence within commercially available expression vector pGEX-2T. This sequence is derived from *Schistosoma japonicum*. A number of species are known to produce active isoforms of Gst, all of which are useful in the present invention.

Coding regions for the fusion protein may be spliced into an expression vector by means well understood by those having ordinary skill in the art. Suitable expression vectors may be constructed using standard recombinant DNA techniques known in the art, many of which are described in Sambrook, et al., *Molecular Cloning: A Laboratory Manual*, Second Edition, Cold Spring Harbor Laboratory, Cold Spring Habor, N.Y. (1989).

Suitable expression vectors in accordance with the present invention comprise a coding region for a polypeptide capable of binding to glutathione, along with an in-frame sequence for the protein to be isolated. The coding region for the protein to be isolated may be located upstream or downstream of the coding region for the glutathione-binding polypeptide. Preferred are expression vectors comprising one or more regulatory DNA sequences operatively linked to the DNA sequence coding for all or part of Gst.

Expression vectors useful in the present invention typically contain an origin of replication, a promoter located 5' to (i.e., upstream of) the Gst fusion protein sequence, which is followed by downstream transcription termination sequences, and the remaining vector. Control regions derived from a number of sources may be employed in accordance with the present invention. Suitable origins of replication include, for example, the Col E1, the SV40 viral and the M13 orgins of replication. Suitable promoters include, for example, the cytomegalovirus promoter, the lac Z promoter, the gal 10 promoter and the *Autographa californica* multiple nuclear polyhedrosis virus (AcMNPV) polyhedral promoter. Suitable termination sequences include, for example, SV40, lac Z and AcMNPV polyhedral polyadenylation signals. An expression vector as contemplated by the present invention is at least capable of directing the replication, and preferably the expression, of the nucleic acids encoding the fusion proteins.

The expression vectors may also include other DNA sequences known in the art; for example, stability leader sequences which provide for stability of the expression product; secretory leader sequences, which provide for secretion of the expression product; sequences that allow expression of the structural gene to be modulated (e.g., by the presence or absence of nutrients or other inducers in the growth medium); marking sequences, which are capable of providing phenotypic selection in transformed host cells (e.g., genes for neomycin, ampicillin, and hygromycin resistance and the like); and sequences that provide sites for cleavage by restriction endonucleases. All of these materials are known in the art and are commercially available.

The characteristics of the actual expression vector used must be compatible with the host cell to be employed. The vector thus may include sequences which allow expression in various types of host cells, including but not limited to prokaryotes, yeasts, fungi, plants and higher eukaryotes. For example, when expressing DNA sequences in a mammalian cell system, the expression vector should contain promoters isolated from the genome of mammalian cells, (e.g., mouse metallothionien promoter), or from viruses that grow in these cells (e.g., baculovirus promoter, vaccinia virus 7.5 K promoter).

Suitable commercially available expression vectors into which DNA sequences for the fusion proteins may be inserted include the mammalian expression vectors pcDNAI or pcDNA/Neo, the baculovirus expression vectors pBlue-Bac and pVL1393 (which is preferred), the prokaryotic expression vector pcDNAII and the yeast expression vector pYes2, all of which may be obtained from Invitrogen Corp., San Diego, Calif. Preferred are commercially available vectors that already have Gst sequences included, such as pGEX-2T.

The present invention additionally concerns host cells containing an expression vector that comprises a DNA sequence coding for a Gst fusion protein. The host cells preferably contain an expression vector which comprises all or part of the DNA sequence for the protein to be isolated together with a DNA sequence for a polypeptide capable of binding glutathione. See, for example, the expression vector appearing in the Experimental Procedures hereinbelow, which is preferred. Further preferred are host cells containing an expression vector comprising one or more regulatory DNA sequences capable of directing the replication and/or the expression of and operatively linked to a DNA sequence coding for all or part of the fusion protein. Suitable host cells include both prokaryotic and eukaryotic cells. Suitable prokaryotic host cells include, for example, *E. coli* strains HB101, DH5α, XL1 Blue, Y1090 and JM101. Suitable eukaryotic host cells include, for example, *Spodoptera frugiperda* insect cells (which are preferred), COS-7 cells, human skin fibroblasts, and *Saccharomyces cerevisiae* cells.

Expression vectors may be introduced into host cells by various methods known in the art. For example, transfection of host cells with expression vectors can be carried out by the calcium phosphate precipitation method. However, other methods for introducing expression vectors into host cells, for example, electroporation, liposomal fusion, nuclear injection, and viral or phage infection can also be employed.

Once an expression vector has been introduced into an appropriate host cell, the host cell may be cultured under conditions permitting expression of large amounts of the fusion protein.

BRIEF DESCRIPTION OF THE FIGURES

FIGS. 1A–1B: Construction of pBMS-I

A. Outline of the cloning procedure. The glutathione-s-transferase gene was cloned into the Bam H-1 site of the Sf9 expression vector pVL1393 to make the Gst fusion expression vector pBMS-I. The restriction map of the pBMS-I polylinker, and the thrombin cleavage site are shown. The DNA sequence at the bottom of FIG. 1A is designated SEQ ID NO:.5. The amino acid sequence at the bottom of FIG. 1A is designated SEQ ID NO:.6.

B. Schematic of the GstLck fusion junction. lck was joined to the Gst coding sequence using a Stu-1 site located 24 base pairs upstream of the lck intiation methionine codon. The DNA sequence at bottom of FIG. 1B is designated SEQ ID NO:.7. The amino acid sequence at the bottom of FIG. 1B is designated SEQ ID NO:.8.

FIGS. 2A–2C: Analysis of GstLck purified from Sf9 cells.

A. SDS-PAGE analysis and Coomassie staining pattern. Lane 1 shows the result from 50 μg of total protein from infected Sf9 cells; lane 2, 1 μg of purified GstLck; lane 3, 0.5 μg of thrombin-cleaved GstLck (recombinant $p56^{lck}$).

B. SDS-PAGE analysis of autophosphorylated GstLck. Lane 1 shows the result from autophosphorylation of GstLck; lane 2, autophosphorylation of recombinant $p56^{lck}$.

C. Western blot analysis of the sample used in panel B using a polyclonal rabbit anti-lck antibody. Lane 1 shows the result from GstLck; Lane 2, recombinant $p56^{lck}$.

FIGS. 3A–3B: Autophosphorylation of GstLck.

A. Western blot analysis of $p56^{lck}$. Lane 1 shows the result from immunoprecipitated $p56^{lck}$ from CEM-6 cells; lanes 2–4, GstLck from infected Sf9 cell lysates purified using the following methods. Lane 2, immunoprecipitation using anti-lck polyclonal antibodies; lane 3, immunoprecipitation using anti-Gst polyclonal antibodies; lane 4, affinity purification using glutathione resin.

B. Analysis of the enzymatic activity of $p56^{lck}$ or GstLck purified as outlined in panel A. Activity was assessed by autophosphorylation. The same protein samples and quantities were loaded as in panel A.

FIGS. 4A–4B: Phosphorylation of enolase by GstLck.

A. Phosphorylation of enolase as a function of GstLck concentration. Each reaction was carried out for 1 minute at 30° C., with 3 μg of enolase as substrate, and varying amounts of GstLck. Lane 1 shows the result from 0 μg GstLck; Lane 2, 0.04 μg GstLck, lane 3, 0.08 μg GstLck; lane 4, 0.12 μg GstLck; lane 5, 0.2 μg GstLck; lane 6, 0.28 μg GstLck; lane 7, 0.36 μg GstLck; lane 8, 0.44 μg GstLck; lane 9, 0.52 μg GstLck.

B. Time course of enolase phosphorylation by GstLck. Each reaction was carried out at 30° C., with 0.4 μg of GstLck, and 3 μg of enolase as substrate. Lane 1 shows the result after 0 minutes; lane 2, 0.5 minute; lane 3, 1 minute; lane 4, 2 minutes; lane 5, 3 minutes.

FIGS. 5A–5B: Phosphorylation of enolase by thrombin-cleaved GstLck.

A. Phosphorylation of enolase as a function of recombinant $p56^{lck}$. Each reaction was carried out for 1 minute at 30° C., with 3 μg of enolase as substrate, and varying amounts of recombinant $p56^{lck}$. Lane 1 shows the result from 0 μg $p56^{lck}$; lane 2, 0.01 μg $p56^{lck}$; lane 3, 0.02 μg $p56^{lck}$; lane 4, 0.03 μg $p56^{lck}$; lane 5, 0.05 μg $p56^{lck}$; lane 6, 0.07 μg $p56^{lck}$; lane 7, 0.09 μg $p56^{lck}$; lane 8, 0.11 μg $p56^{lck}$.

B. Time course of enolase phosphorylation by recombinant $p56^{lck}$. Each reaction was carried out at 30° C., with 0.01 μg of recombinant $p56^{lck}$, and 3 μg of enolase as substrate. Lane 1 shows the result after 0 minutes; lane 2, 0.5 minutes; lane 3, 1 minute; lane 4, 2 minutes; lane 5, 3 minutes.

DETAILED DESCRIPTION OF THE PREFERRED EMBODIMENT

Experimental Procedures

Construction of $p56^{lck}$ expression vectors. A Stu-1 fragment from the mouse lck cDNA (Marth, J. D., Peet, R., Krebs, E. G., and Perlmutter, R. (1985) *CELL*, 393–404) was cloned into the filled-in Eco-R1 site of the vector pGEX-2T (Pharmacia). The resulting plasmid pGEX-lck, is capable of expressing a glutathione-s-transferase/Lck (GstLck) fusion protein when transfected into *E. coli* cells. The GstLck coding sequence from pGEX-lck was amplified by PCR. The 5' PCR primer

5' TAT AAA TAT GTC CCC TAT ACT A 3'
(SEQ. ID. NO.: 3), was synthesized on an Applied Biosystems, Inc. model 380A synthesizer. This primer hybridizes to the 5' region of the Gst coding sequence and encodes the ribosome binding site for the baculovirus polyhedrin gene. The 3' PCR primer,

5' CGT CAG TCA GTC ACG AT 3'
(SEQ. ID. NO.: 4), hybridizes to sequences immediately 3' to the polylinker of pGEX-2T. This primer pair can be used to amplify any sequence cloned into the polylinker of pGEX-2T as a Gst/insert fusion. The amplified GstLck coding sequence was cloned into the vector pCR1000 (InVitrogen, Inc.) resulting in the plasmid pCR1000-GstLck. The pCR1000 vector was designed for easy cloning of PCR-amplified DNA, and was used as an intermediate cloning vector. A Not-1, BgI-II fragment from pCR1000-GstLck containing GstLck coding sequence was cloned into the Not-I, BgI-II sites of pVL1393. Lukow, V. A., and Summers, M. D. (1988) Virology 167, 56–71. The resulting plasmid, pVL1393-GstLck was used to produce a recombinant baculovirus in *Spodoptera frugiperda* 9 (Sf9) cells following standard procedures. Summers, M. D., and Smith, G. E. (1987). *A Manual for baculovirus vectors and insect cell culture procedures*, Texas A&M bulletin No. 1555, (College Station, Tex. Agricultural Experimental Station and Texas A&M University), 10–39. The cloning scheme used for the construction of pBMS-I is outlined in FIG. 1A. The PCR primers used are the same described above.

Purification of GstLck from Sf9 cells. A 500 mL spinner culture of infected Sf9 cells in Excell-400 medium (JRH Biosciences) was harvested 48 hours after infection by centrifugation at 4° C. for 5 minutes. The cells were lysed in 50 mL of cold 50 mM Tris pH 8.0, 150 mM NaCI, 2 mM EDTA, 1 mM DTT, 1%(vol/vol) NP-40, 1 mM PMSF, 0.1 mg/mL aprotinin, 0.1 mg/mL leupeptin, 1 mM NaF, and 1 mM $Na_3VO_4$ (lysis buffer). Insoluble material was removed by centrifugation at 10,000×g for 10 minutes at 4° C. The resulting cell lysate was determined to have a protein concentration of 9.5 mg/mL using the Coomassie Protein Assay Reagent (Pierce).

The GstLck protein was purified by a one-step affinity chromatograpy procedure using glutathione resin as described by the manufacturer (Pharmacia). For this experiment, 50 mg of Sf9 cellular lysate containing the GstLck protein was added to a 2-mL glutathione column and the unbound material removed by washing with 50 mL of lysis buffer. Bound proteins were eluted from the column with 2 column volumes of lysis buffer containing 5 mM glutathione. Eluted protein was diluted to 15 mL with lysis buffer and concentrated using a Centriprep 30 Concentrator unit (Amicon, Inc.). Two additional dilutions and concentrations were performed to remove the remaining glutathione. The concentrated protein was adjusted to 10% glycerol and stored at −70° C. This procedure yielded 28.0 mg of greater than 99% pure GstLck as determined by SDS-PAGE and Coomassie Blue staining analysis.

To obtain $p56^{lck}$ protein lacking the Gst peptide sequences, GstLck was digested with the proteolytic enzyme thrombin to generate cleaved $p56^{lck}$ ($cp56^{lck}$). For this procedure 5 mg of thrombin was added to 20 mg of purified GstLck in a volume of 50 mL lysis buffer, containing 2.5 mM $CaCl_2$ for 1 hour at 25° C. To remove uncleaved GstLck and cleaved Gst, the products were mixed with 20 mL of glutathione resin. The glutathione resin was removed by centrifugation leaving the $cp56^{lck}$ in the supernatant. The yield from this procedure was approximately 5 mg of recombinant $p56^{lck}$ which was stored in 10% glycerol at −70° C.

Immune-complex protein kinase assays. Analysis of protein kinase activity conducted on immune-complexes was carried out as previously described. Veillette, A., Horak, I. D., Horak, E. M., Bookman, M. A., and Bolen, J. A. (1988) *Mol. Cell. Biol.* 8, 4353–4361. Briefly, immune-complexes formed from cellular lysates and the indicated antisera were collected by the addition of formalin-fixed *Staphyloccocus aureus* (Pansorbin, Calbiochem) and washed extensively in lysis buffer. Protein kinase reactions were initiated by the addition of 30 mL kinase buffer (20 mM MOPS pH 7, 5 mM $MnCl_2$, 1 mM ATP) containing 12.5 $\mu$Ci [$\gamma$-$^{32}$P]-ATP (3000 Ci/mmol, New England Nuclear). The reactions were allowed to proceed for 5 minutes at room temperature and stopped by addition of an equal volume of 2ЗЗ SDS loading buffer (0.125 M Tris-HCl pH 6.8, 4% (weight/vol) SDS, 20% (vol/vol) glycerol, 10% (vol/vol) 2-mercaptoethanol). The phosphorylated products in SDS loading buffer were heated for 5 minutes at 90° C. and analyzed by SDS-PAGE and autoradiography. The 32P-labeled bands of interest were excised from the gel and counted in a Beckman LS6000TA liquid scintillation counter.

Soluble protein kinase assays. The enzymatic activity of GstLck and $cp56^{lck}$ were evaluated by their capacity to phosphorylate the Lck exogenous substrate rabbit muscle enolase (Sigma). To determine the time course of enolase phosphorylation, 3 $\mu$g of GstLck or 1 $\mu$g of $cp56^{lck}$ was added to 100 $\mu$l of kinase buffer containing 12 $\mu$g enolase and 25 $\mu$gCi [$\gamma$-$^{32}$P]-ATP and the reactions were conducted at 30° C. for the indicated times. At each point, 10 $\mu$L of the reaction mix was removed, added to 30 $\mu$L of 2×SDS loading buffer and heated for 5 minutes at 90° C. The reaction products were analyzed by SDS-PAGE and autoradiography. The bands corresponding to enolase were excised from the gel and counted by liquid scintillation spectroscopy. To determine the $K_m$ for enolase, serial dilutions of enolase were added to kinase buffer containing 5 $\mu$Ci [$\gamma$-$^{32}$P]-ATP, and either 0.1 $\mu$g of GstLck or 0.01 $\mu$g of $cp56^{lck}$ were added per reaction. Reaction conditions and the counts incorporated into enolase were determined as described above. For the $K_m$ determination of ATP, a 1:10 dilution of [$\gamma$-$^{32}$P]-ATP was added to kinase buffer containing 3 $\mu$g enolase. For each ATP dilution, 1 $\mu$g of $cp56^{lck}$ was added in a total volume of 30 $\mu$L and reacted for 30 seconds at 30° C. Reactions were stopped by addition of 30 $\mu$L of 2×SDS loading buffer and heated to 90° C. The reaction products were analyzed by SDS-PAGE, the phosphorylated proteins visualized by autoradiography, and $^{32}$P incorporation determined by liquid scintillation spectroscopy of the excised bands.

Other biochemical assays and materials. Lck immunoblot analysis was conducted as previously described using rabbit anti-lck antisera. Veillette, A., Bookman, M. A., Horak, E. M., and Bolen, J. A. (1988)*CELL* 55, 301–308. Partial proteolytic peptide analysis using *Staphylococcus aureus* V8 protease (Pierce) has also been previously described. Veillette, A., Horak, I. D., Horak, E. M., Bookman, M. A., and Bolen, J. A. (1988) *Mol. Cell. Biol.*, 4353–4361; Marth, J. D., Cooper, J. A., King, C. S., Ziegler, S. F., Tinker, D. A., Overell, R. A., Krebs, E. G., and Perlmutter, R. M. (1988) *Mol. Cell. Biol.*, 540–550. The human T-cell lymphoma cell line CEM was grown in RPM1 1640 media supplemented with 10% (vol/vol) fetal bovine serum and antibiotics (penicillin/streptomycin). For immunoprecipitation experiments, the cells were washed in phosphate buffered saline, collected by centrifugation, lysed in lysis buffer, and adjusted to 1 mg/ml prior to addition of anti-Lck antisera. Antisera directed against Gst was prepared by immunization of rabbits with purified Gst. Antisera directed against Lck amino acids 39–58 has been previously described. Veillette, A., Bookman, M. A., Horak, E. M., and Bolen, J. A. (1988) *Cell* 55, 301–308.

Results

Figure 1A:
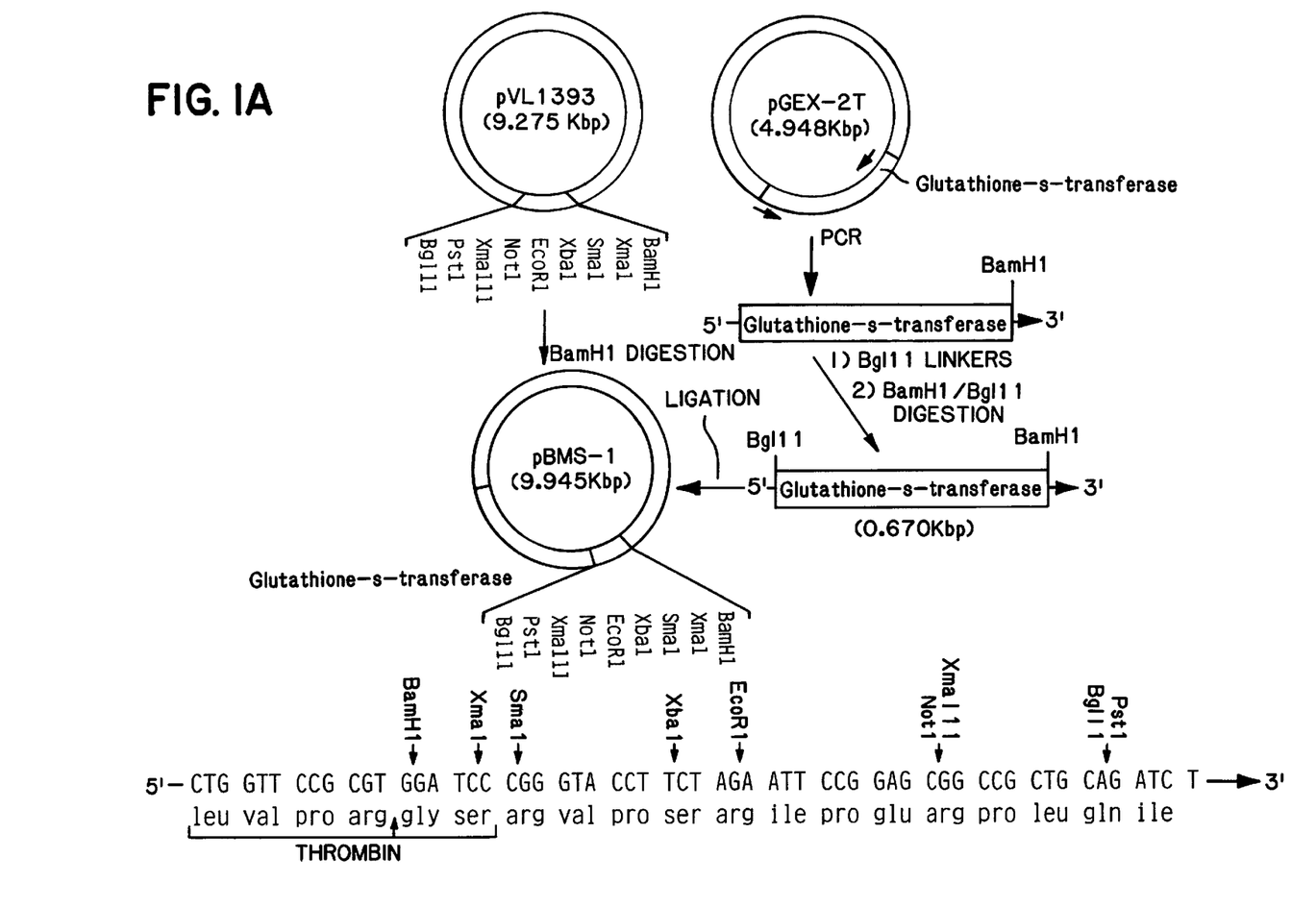

Construction of expression vectors. FIG. 1A outlines the cloning strategy used to create the expression vector pBMS-I. The Gst coding sequence from pGEX-2T was cloned by PCR amplification, and ligated into the baculovirus expression vector pVL1393. The 5' PCR primer was designed to optimize translation of the Gst coding sequence in Sf9 cells. This was accomplished by changing the sequence surrounding the initiation methionine of Gst to encode the ribosomal binding site of the baculovirus polyhedrin gene. The pBMS-I polylinker contains 9 unique cloning sites, and can be used to make a recombinant baculovirus that expresses inserts as a Gst fusion protein in Sf9 cells.

Figure 1B:
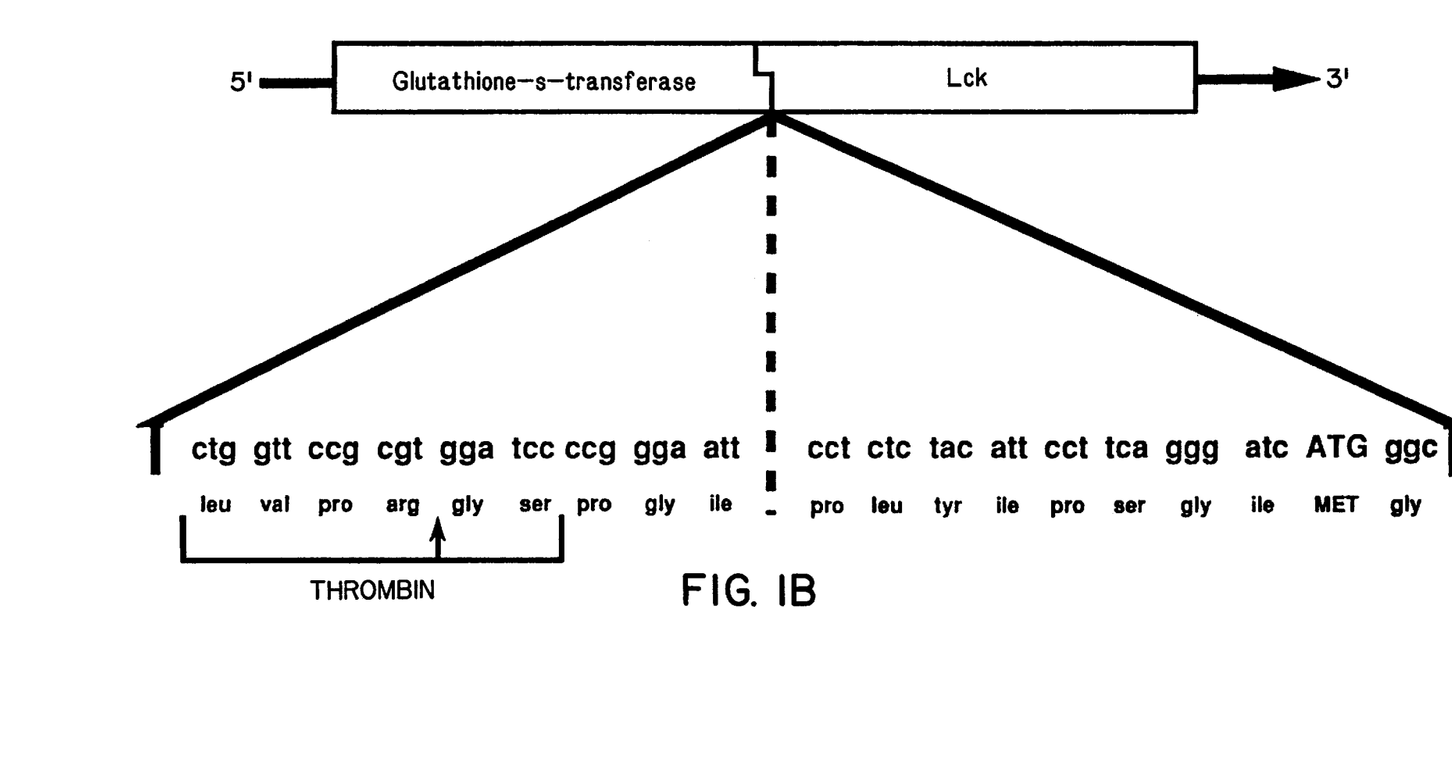

The fusion junction of the GstLck coding sequences cloned into pVL1393 is schematically shown in FIG. 1B. The thrombin cleavage site is also indicated. This plasmid pVL1393-GstLck was used to make a recombinant baculovirus that expressed high levels of the GstLck fusion protein in Sf9 cells. Thrombin cleavage of GstLck protein resulted in a recombinant p56$^{lck}$ (cp56$^{lck}$) molecule containing an additional 13 amino acids at the Lck amino-terminus. These additional amino acids had no apparent affect on the in vitro enzymatic activity of recombinant p56$^{lck}$. This was determined by comparing the immune-complex protein kinase activities of cp56$^{lck}$ with that of wild-type p56$^{lck}$ expressed in Sf9 cells.

Figure 2A:
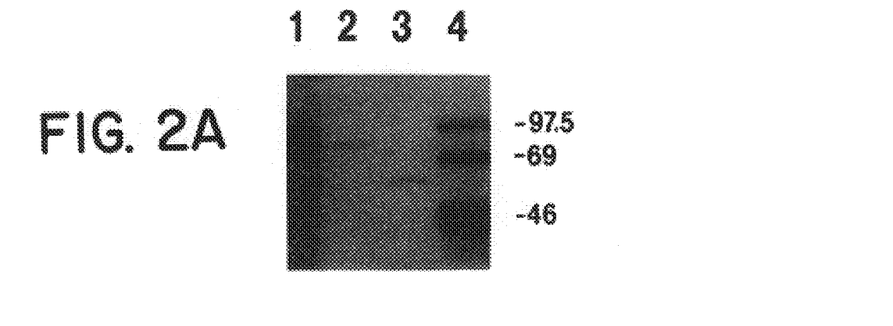

Purification of GstLck from Sf9 cells. Total detergent lysates were made from Sf9 cells expressing the GstLck fusion protein as outlined in Experimental Procedures. Lysate containing GstLck was bound to a glutathione-sepharose column and eluted with 5 mM glutathione in lysis buffer. The glutathione-bound products from this column were analyzed by Coomassie staining following fractionation on SDS polyacrylamide gels. As shown in FIG. 2A, a single polypetide of approximately 83 kDa was observed which corresponds to the expected size for the GstLck fusion protein. Following thrombin cleavage (FIG. 2A, lane 3), the recombinant Lck protein was observed to migrate as two closely spaced bands at approximately 56 kDa.

Figure 2B:
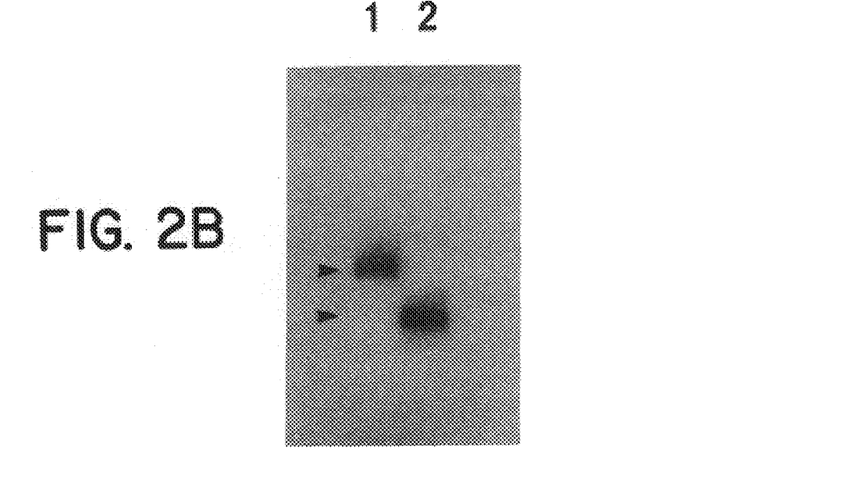
Figure 2C:
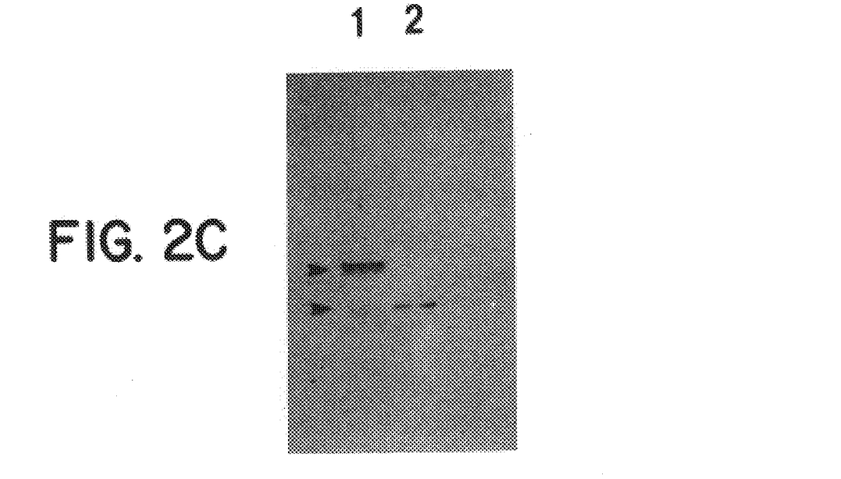

Functional analysis of GstLck and cp56$^{lck}$. To evaluate the kinase activity of the purified GstLck and cp56$^{lck}$ proteins, protein kinase assays were performed. The results of these reactions (FIG. 2B) demonstrated that purified GstLck and cp56$^{lck}$ maintained their autophosphorylation capacity. As expected, no kinase activity was detected in purified preparations of Gst. The data shown in FIG. 2C represents the corresponding Lck immunoblot using polyclonal rabbit antibodies against the p56$^{lck}$ unique region. Based on the relative amounts of Lck protein detected in the kinase reactions, it appears that the specific activity of the cp56$^{lck}$ may be slightly higher than that of the GstLck fusion protein. Anti-phosphotyrosine immunoblot analysis of similar reaction products generated using non-radioactive ATP demonstrated that the autophosphorylation products (as well as the phosphorylation of exogenous protein substrate enolase used in other experiments) were phosphorylated on tyrosine residues. Additionally, partial V8 peptide analysis of the autophosphorylation products of the GstLck and cp56$^{lck}$ reactions yielded major V8 phosphopeptides indistinguishable from that of T-cell derived p56$^{lck}$ autophosphorylated in immune-complex kinase assays.

Figure 3A:
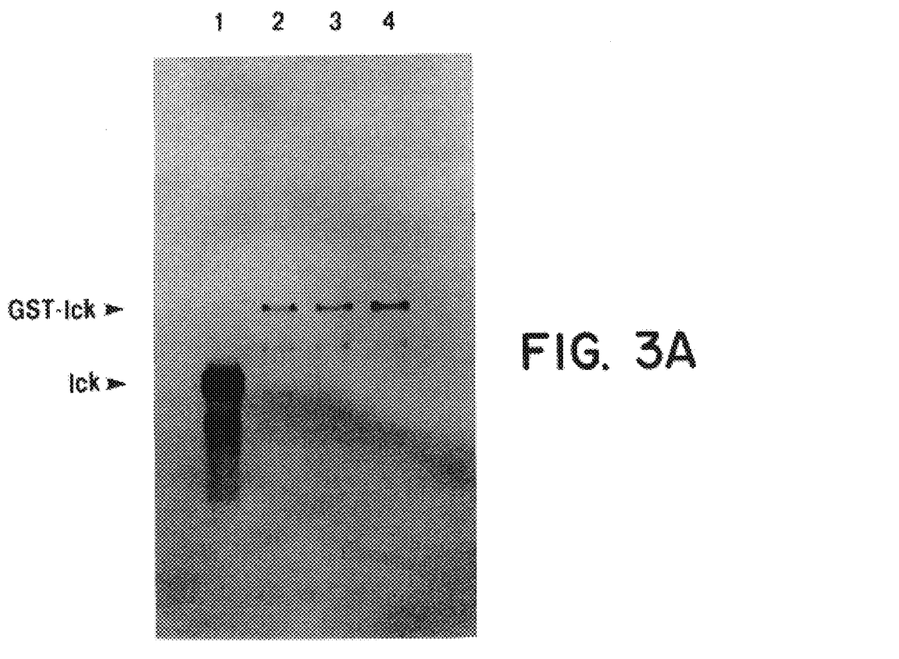
Figure 3B:
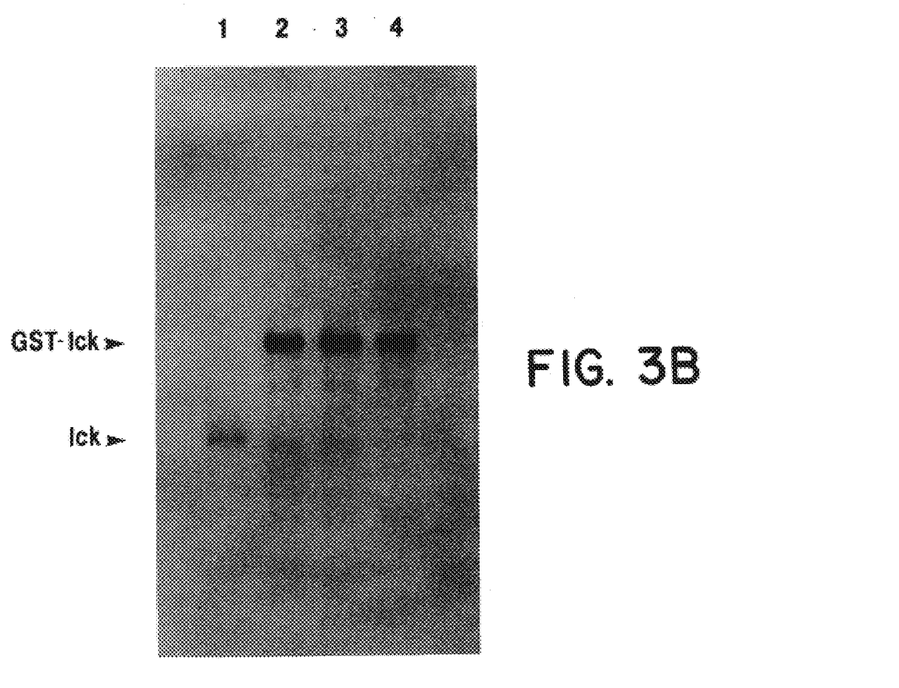
Figure 4A:
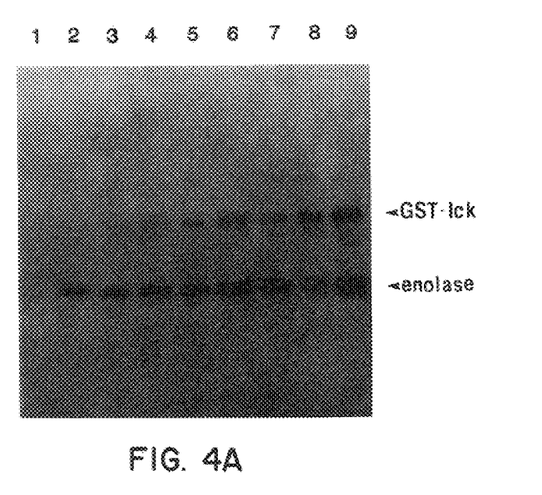
Figure 4B:
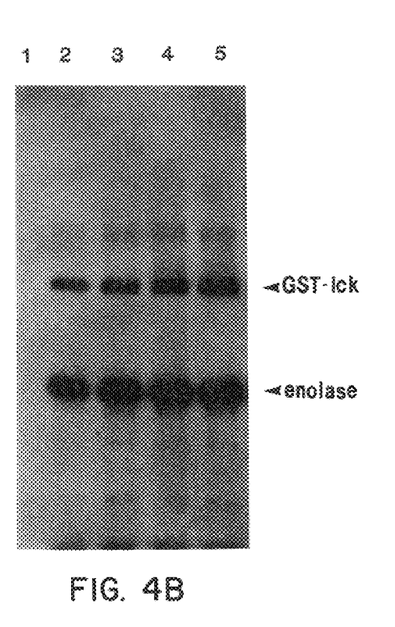

The level of GstLck enzymatic activity was also compared to that of wild type p56$^{lck}$ immunoprecipitated from T-cell detergent lysates. For these experiments, GstLck was precipitated from infected Sf9 detergent lysates with anti-Lck antisera, anti-Gst antisera, or with glutathione-Sepharose beads. The p56$^{lck}$ from T-cell lysates was immunoprecipitated with anti-Lck antisera. The various complexes were washed extensively with lysis buffer and divided into two equal aliquots. One aliquot was used to perform protein kinase assays (FIG. 3B) while the other aliquot was used for Lck immunoblot analysis (FIG. 3A). The results of this experiment demonstrate that precipitation of the GstLck protein using either antibodies or glutathione beads yielded molecules with similar specific activities as assessed by autophosphorylation. Comparison with p56$^{lck}$ derived from T-cells showed that the specific activity of the Sf9 derived GstLck protein was significantly higher.

Figure 5A:
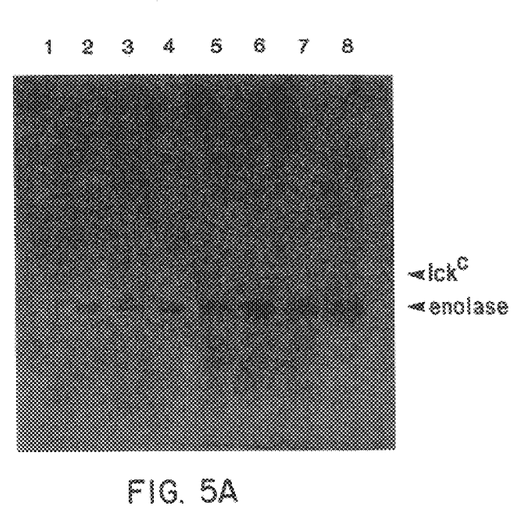
Figure 5B:
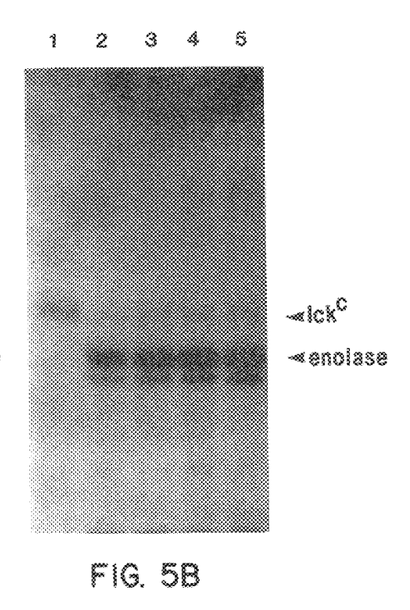

To further characterize the kinetic parameters of GstLck and cp56$^{lck}$, kinase activity of the fusion protein and cleaved enzyme was studied using rabbit muscle enolase as an exogenous substrate. As shown by the data presented in FIG. 4, the phosphorylation of enolase by GstLck was found to be both time and concentration dependent. Similar results were obtained for cp56$^{lck}$ (FIG. 5). The $K_m$ and $V_{max}$ values for ATP and enolase were determined using a reaction time of 30 seconds and the results summarized in Table 1. The affinity of cp56$^{lck}$ for enolase was found to be approximately 10-fold higher then that of GstLck. More critically the $K_m$ and $V_{max}$ values determined for cp56$^{lck}$ are comparable to values obtained for other src family members.

Attempts to produce functional GstLck in *E. coli* were unsuccessful. The resulting fusion protein was expressed, but it lacked detectable protein kinase activity and was found to be insoluble in detergents. The latter feature is common to expression of many eukaroytic proteins in bacteria. Marston, A. O. (1986) *J. Biochem*, 240, 1–12; Miller, D. W., Saher, P., and Miller, L. K. (1986) in *Genetic Engineering*, vol. 8, pp. 277–298, Plenum, N.Y.; Miller, L. K. (1989) in Ann. Rev. Microbiol. 42, 177–199. Among the advantages of expression of eukaryotic proteins in Sf9 cells is the capacity of these cells to allow protein folding and post-translational modification that maintain protein solubility. In the case of Lck, expression of the wild-type p56$^{lck}$ in Sf9 cells using conventional baculovirus expression vectors has shown that Lck is myristylated and phosphorylated on serine and threonine residues. Thomas, J. E., Soriano, P., and Brugge, J. S. (1991) *Science* 254,.568–571. Since Lck in this system is expressed as a fusion protein with Gst at the aminoterminus, it is unlikely that myristylation occurs. We have not determined whether the GstLck is phosphorylated on serine or threonine residues.

Discussion

The lck coding sequences were ligated downstream from the Gst coding region in-frame to yield a plasmid capable of encoding a Gst-p56$^{lck}$ fusion protein. The p56$^{lck}$ produced in this manner was found to be a highly active protein kinase, and exhibited the expected biochemical properties of a member of the src family.

Analysis of both the GstLck fusion protein as well as the cp56$^{lck}$ indicated that each retained significant protein tyrosine kinase activity as measured by autophosphorylation and tyrosine phosphorylation of the exogenous substrate rabbit muscle enolase. Importantly, the Gst sequences, whether fused to Lck or following cleavage from the kinase with thrombin, were not phosphorylated in immune-complex kinase assays or in kinase assays conducted in solution. Both the GstLck and the cp56$^{lck}$ were found to have substantially higher specific activities than p56$^{lck}$ derived from T-cells when measured by immune-complex protein kinase assays. The altered specific activity is likely to be the result of diminished carboxy-terminal tyrosine (tyrosine 505) phosphorylation for Lck in Sf9 cells although we have not determined the phosphorylation sites of Lck in these cells. Veillette, A., Horak, I. D., Horak, E. M., Bookman, M. A., and Bolen, J. A. (1988) *Mol. Cell. Biol.* 8, 4353–4361; Marth, J. D., Cooper, J. A., King, C. S., Ziegler, S. F., Tinker, D. A., Overell, R. A., Krebs, E. G., and Perlmutter, R. M. (1988) *Mol. Cell. Biol.* 8, 540–550. The lack of tyrosine 505 phosphorylation of Lck like that observed with Sf9-derived pp60$^{c-src}$ (Morgan, D. O., Kaplan, J. M., Bishop, J. M., and Varmus, H. E. (1989)*CELL* 57, 775–786), is probably attributable to the absence of expression of other tyrosine protein kinases such as Csk that are thought to phosphorylate the Src class of kinases at this site. Okada, M., and Nakagawa, H. (1989) *J. Biol. Chem.* 264, 20886–20893; Okada, M., and Nakagawa, H. (1988) *Biochem. Biophys. Res. Commun.* 154, 796–7636 802.

From 50 mg of total 29 protein lysate, the foregoing procedure purified 280 mg of greater than 99% pure (by silver and Coomassie staining) recombinant p56$^{lck}$. From one liter of infected Sf9 cells, this system produced approximately 8–10 mg of purified recombinant Lck.

The foregoing procedures were also used to produce GstLynB, GstSyk, GstBlk, GstFyn, and GstYes fusion proteins with comparable results and yields to that reported here for Lck. These results are reported below in Tabel I.

The abbreviations used throughout this specification are defined as follows.

| | |
|---|---|
| ATP | adenosine triphosphate |
| DNA | deoxyribonucleic acid |
| DTT | dithiothreitol |
| MOPS | (3-[N-morpholino]propanesulfonic acid) |
| PCR | polymerase chain reaction |
| PAGE | polyacrylamide gel electrophoresis |
| PMSF | phenylmethylsulfonyl fluoride |
| SDS | sodium dodecyl sulfate |

The gene for GST can be cleaved by enzymes at the positions ("Pos.") shown in Table 2. Such nucleic acid fragments can be used to generate partial Gst polypeptides in the fusion proteins of the present invention.

| | |
|---|---|
| 11 | EcoN1 |
| 13 | Bfa1 |
| 13 | BsiY1 |
| 13 | Bs11 |
| 13 | Mae1 |
| 13 | Rma1 |
| 17 | BsmF 1 |
| 26 | EcoR1* |
| 26 | Tsp509 1 |
| 29 | Mse1 |
| 33 | Asu1 |
| 33 | BsiZ1 |
| 33 | Cfr13I |
| 33 | Dra11 |
| 33 | Eco0109I |
| 33 | Nsp1V |
| 33 | Sau96I |
| 35 | BsuR1 |
| 35 | Hae111 |
| 35 | Pa11 |
| 36 | Pss1 |
| 51 | Taq1 |
| 51 | TthHB81 |
| 65 | Bcq1 |
| 80 | Eam11041 |
| 80 | Ear1 |
| 80 | Ksp6321 |
| 85 | Mbo11 |
| 95 | Ms1 1 |
| 97 | Mbo11 |
| 102 | Hin61 |
| 102 | HinP11 |
| 102 | HinP1 |
| 104 | Acc11 |
| 104 | Bsh1236 1 |
| 104 | Bsp501 |
| 104 | BstU1 |
| 104 | Cfo1 |
| 104 | FnuD11 |
| 104 | Hha1 |
| 104 | Mvn1 |
| 104 | Tha1 |
| 121 | AciI |
| 124 | Hph1 |
| 139 | EcoR1* |
| 139 | Tsp509 1 |
| 154 | Mbo11 |
| 188 | Mse1 |
| 190 | EcoR1* |
| 190 | Tsp509 1 |

-continued

| | |
|---|---|
| 193 | Hph1 |
| 193 | Mse1 |
| 205 | BsmA1 |
| 206 | Cfr1 |
| 206 | Eae1 |
| 208 | Ba11 |
| 208 | BsuR1 |
| 208 | Hae111 |
| 208 | Msc1 |
| 208 | Pa11 |
| 216 | Mae11 |
| 226 | Alu1 |
| 239 | Af1111 |
| 243 | Nla111 |
| 243 | Nsp75241 |
| 243 | NspH1 |
| 243 | Nsp1 |
| 287 | Bsq1 |
| 292 | BsrB 1 |
| 319 | Taq1 |
| 319 | TthHB81 |
| 323 | EcoR1* |
| 323 | Tsp509 1 |
| 333 | BsmA1 |
| 367 | Dde1 |
| 375 | Alu1 |
| 394 | Asp7001 |
| 394 | Xmn1 |
| 398 | Asu11 |
| 398 | Bpu141 |
| 398 | BsiC1 |
| 398 | Bsp1191 |
| 398 | BstB1 |
| 398 | Csp451 |
| 398 | Lsp1 |
| 398 | Nsp7524V |
| 398 | NspV |
| 398 | Sfu1 |
| 398 | Taq1 |
| 398 | TthHB81 |
| 402 | BspA1 |
| 402 | Dpn11 |
| 402 | Kzo91 |
| 402 | Mbo1 |
| 402 | Nde11 |
| 402 | Sau3A1 |
| 404 | Dpn1 |
| 412 | Mbo11 |
| 427 | Mse1 |
| 428 | Aha111 |
| 428 | Dra1 |
| 428 | SwaI |
| 434 | Fba1 |
| 434 | Fok1 |
| 435 | Bc11 |
| 435 | BsiQ1 |
| 435 | BspA1 |
| 435 | Dpn11 |
| 435 | Kzo91 |
| 435 | Mbo1 |
| 435 | Nde11 |
| 435 | Sau3A1 |
| 437 | Dpn1 |
| 440 | Fba1 |
| 441 | Mae111 |
| 442 | Nla111 |
| 445 | Hph1 |
| 462 | Nla111 |
| 478 | Hga1 |
| 495 | Af11 |
| 495 | Asu1 |
| 495 | Ava11 |
| 495 | Bme181 |
| 495 | BsiZ1 |
| 495 | Cfr13I |
| 495 | Eco47I |
| 495 | Eco471 |
| 495 | Nla111 |
| 495 | NspH11 |

-continued

| | |
|---|---|
| 495 | Nsp1V |
| 495 | Sau96I |
| 495 | Sin1 |
| 497 | BscB1 |
| 497 | NlaIV |
| 501 | SfaN1 |
| 506 | DsaV |
| 506 | EcoR11 |
| 508 | Apy1 |
| 508 | BsiL1 |
| 508 | BstN1 |
| 508 | BstO1 |
| 508 | Mval |
| 508 | ScrF1 |
| 523 | EcoR1* |
| 523 | Fok1 |
| 523 | Tsp509 1 |
| 536 | Mse1 |
| 537 | Aha111 |
| 537 | Dra1 |
| 543 | Mae11 |
| 553 | Alu1 |
| 563 | EcoR1* |
| 563 | Tsp509 1 |
| 573 | Csp61 |
| 574 | Afa1 |
| 574 | Rsa1 |
| 574 | Sca1 |
| 602 | Nla111 |
| 603 | BsuR1 |
| 603 | Hae111 |
| 603 | Pa11 |
| 610 | BsiY1 |
| 610 | Bs11 |
| 615 | BspW1 |
| 615 | Mwo 1 |
| 625 | Mae11 |
| 629 | Fok1 |
| 636 | AciI |
| 656 | Mn11 |
| 657 | BspA1 |
| 657 | BstY1 |
| 657 | Dpn11 |
| 657 | Kzo91 |
| 657 | Mbo1 |
| 657 | Mf11 |
| 657 | Nde11 |
| 657 | Sau3A1 |
| 657 | Xho11 |
| 659 | Dpn1 |
| 665 | Alw1 |
| 665 | BscB1 |
| 665 | NlaIV |
| 667 | AciI |
| 668 | Alw1 |
| 669 | Acc11 |
| 669 | Bsh1236 1 |
| 669 | Bsp501 |
| 669 | BstU1 |
| 669 | FnuD11 |
| 669 | Mvn1 |
| 669 | Tha1 |
| 673 | BamH1 |

-continued

| | |
|---|---|
| 673 | BspA1 |
| 673 | BstY1 |
| 673 | Dpn11 |
| 673 | Kzo91 |
| 673 | Mbo1 |
| 673 | Mf11 |
| 673 | Nde11 |
| 673 | Sau3A1 |
| 673 | Xho11 |
| 675 | BscB1 |
| 675 | Dpn1 |
| 675 | NlaIV |
| 677 | BsaJ1 |
| 677 | Bsa11 |
| 677 | DsaV |
| 677 | Sec1 |
| 678 | Aqu1 |
| 678 | Ava1 |
| 678 | Bco1 |
| 678 | BsaJ1 |
| 678 | Bas11 |
| 678 | Cfr91 |
| 678 | DsaV |
| 678 | Eco881 |
| 678 | PspA1 |
| 678 | Sec1 |
| 678 | Xcy1 |
| 678 | Xma1 |
| 679 | Aha1 |
| 679 | Bcn1 |
| 679 | Hap11 |
| 679 | Hpa11 |
| 679 | Msp1 |
| 679 | Nci1 |
| 679 | ScrF1 |
| 680 | Aha1 |
| 680 | Bcn1 |
| 680 | Nci1 |
| 680 | ScrF1 |
| 680 | Sma1 |
| 681 | Alw1 |
| 683 | Apo1 |
| 683 | EcoR1* |
| 683 | EcoR1 |
| 683 | Tsp509 1 |

What is claimed is:

1. An expression vector, comprising:
   (a) a first coding region, which codes for glutathione-S-transferase, operatively connected to a promoter, and
   (b) a restriction region downstream of the first coding region having the sequence of SEQ. ID. NO.:5, which allows for insertion of a second coding region in-frame with the first coding region.

2. The expression vector of claim 1 wherein the code for glutathione-S-transferase has the sequence of SEQ. ID NO.:1.

3. The expression vector of claim 1 wherein the promoter is a baculovirus promoter.

4. A DNA molecule having the sequence of SEQ. ID. NO.:5.

* * * * *